United States Patent [19]

Le Loarer et al.

[11] Patent Number: 5,744,420

[45] Date of Patent: Apr. 28, 1998

[54] ADSORPTION OF CHELATED ORGANOMETALLIC COMPOUNDS ONTO ALUMINA-BASED ADSORBENTS

[75] Inventors: Jean-Luc Le Loarer, Salindres; Christophe Nedez, Asnieres sur Seine, both of France

[73] Assignee: Rhone-Poulenc Chimie, Courbevoie Cedex, France

[21] Appl. No.: 677,562

[22] Filed: Jul. 8, 1996

[30] Foreign Application Priority Data

Jul. 7, 1995 [FR] France ................. 95 08227

[51] Int. Cl.$^6$ ............... B01J 20/00; B01J 23/00; C02F 1/42; B01D 15/04
[52] U.S. Cl. ............... 502/415; 502/341; 502/355; 210/688; 210/691; 210/912; 210/913; 210/914
[58] Field of Search ............... 502/415, 341, 502/355; 210/688, 691, 912, 913, 914

[56] References Cited

U.S. PATENT DOCUMENTS 3,067,128   12/1962   Kimberlin, Jr. et al. ............... 208/138
5,288,849   2/1994   Garcin et al. ............... 528/482

FOREIGN PATENT DOCUMENTS

| 0379394 | 7/1990 | European Pat. Off. | B01J 20/04 |
| 0603990 | 6/1994 | European Pat. Off. | B01J 21/16 |
| 0073525 | 1/1961 | France | C08F 6/02 |
| 3029802 | 3/1981 | Germany | C08F 6/08 |
| 90/04007 | 4/1990 | WIPO | C10G 45/06 |

*Primary Examiner*—Glenn Caldarola
*Assistant Examiner*—In Suk Bullock
*Attorney, Agent, or Firm*—Burns, Doane, Swecker & Mathis, L.L.P.

[57] ABSTRACT

Adsorbent alumina particulates which comprise coagulated droplets, extrudates or crushed alumina particles having a volume of pores with a diameter greater than 80 Å of at least 0.15 cm$^3$/g and a particle size of less than 4 mm are well suited for adsorbing chelated organometallic compound values thereon, in particular from a medium of polymerization comprising same.

20 Claims, No Drawings

ADSORPTION OF CHELATED ORGANOMETALLIC COMPOUNDS ONTO ALUMINA-BASED ADSORBENTS

BACKGROUND OF THE INVENTION

1. Technical Field of the Invention

The present invention relates to the adsorption of chelated organometallic compounds onto alumina-based adsorbents, by contacting said organometallic compounds with an alumina-based adsorbent having judiciously selected characteristics.

This invention also relates to the purification of polyolefins prepared by polymerization of olefins in the presence of coordination catalysts.

The present invention also relates to alumina-based adsorbents, per se, comprising a chelated organometallic compound.

2. Description of the Prior Art

The polyolefins are typically prepared by polymerization of monomers, and optionally of comonomers such as 1-butene, 1-octene, etc., in the presence of polymerization catalysts comprising elements from Groups IVB, VB, VIB of the Periodic Table, and more particularly vanadium, titanium and zirconium. These catalysts also comprise, as reducing agents, organometallic (metal alkyl) compounds, metal hydrides or metal hydroxides. These catalysts, which are generally designated transition catalysts, exhibit great catalytic activity for the polymerization of olefins.

However, once the polymerization is complete, the polyolefins obtained are polluted or contaminated by the metallic residues from the catalysts. Therefore, it is vital to purify these polyolefins prior to using same, to avoid any toxicity, or objectionable coloration or degradation.

In addition, olefin polymerization processes generally comprise a stage of recovery of the monomers which have not reacted during the polymerization and of the solvents present in the polyolefins, these solvents and monomers being recycled into the polymerization reactor. The presence of metals in these compounds promotes, inter alia, corrosion of the reactor apparatus.

To eliminate the metallic residues emanating from the catalysts, one technique entails contacting the medium resulting from the polymerization with organic compounds. This initiates a complexation reaction between the metallic residues and the organic compounds introduced, thus providing chelated organometallic compounds.

Subsequently, to separate these chelated organometallic compounds from the polyolefins, various adsorbents have been employed, especially aluminas.

Among the adsorbents thus employed, adsorbents in the form of beads are representative. These beads are shaped via rotating technology of the film coater or rotating drum type.

SUMMARY OF THE INVENTION

A major object of the present invention is the provision of alumina-based adsorbents for the adsorption of chelated organometallic compounds, which adsorbents exhibit a degree of adsorption which is markedly improved relative to the prior art adsorbents, and especially relative to the alumina beads prepared via a shaping operation employing rotating technology.

Briefly, the present invention features a process for the adsorption of chelated organometallic compounds, comprising contacting said organometallic compounds with an alumina-based adsorbent shaped by coagulation into droplets, or by extrusion or by crushing, said adsorbent having a volume of pores with a diameter greater than 80 Å of at least 0.15 cm$^3$/g and a particle size of less than 4 mm.

This invention also features alumina-based adsorbents, per se, comprising a chelated organometallic compound and prepared via the process described above.

DETAILED DESCRIPTION OF BEST MODE AND PREFERRED/SPECIFIC EMBODIMENTS OF THE INVENTION

More particularly according to the present invention, the subject adsorbents may be employed in various forms.

First, the subject adsorbents may be alumina beads prepared via shaping by coagulation into droplets. This type of bead can be prepared, for example, by a technique as described in EP-B-0,015,801 or EP-B-0,097,539. The porosity can be controlled, in particular, as described in EP-B-0,097,539, by coagulation into droplets of an aqueous dispersion or suspension of alumina or of a solution of a basic aluminum salt which is in the form of an emulsion comprising an organic phase, an aqueous phase and a surfactant or emulsifier. The organic phase may, in particular, be a hydrocarbon, while the surfactant or emulsifier is, for example, Galoryl EM 10®.

The adsorbents may also comprise crushed alumina. These crushed forms may result from the crushing of any type of alumina-based material such as, for example, beads prepared via any type of process (coagulation into droplets, film coater or rotating drum), extrudates, etc. The porosity of these crushed forms if controlled by the selection of the alumina-based material which is crushed.

Lastly, the subject adsorbents may be alumina extrudates. These can be prepared by kneading and then extruding an alumina-based material, which may have been prepared via the rapid dehydration of hydrargillite (flash alumina) or from the precipitation of an alumina gel. The porosity of the extrudates can be controlled by the selection of alumina employed and by the conditions for the preparation of this alumina, or by the operating conditions for the kneading of such alumina prior to extrusion. The alumina can, accordingly, be mixed with pore-forming agents over the course of kneading. For example, the extrudates can be prepared via the process described in U.S. Pat. No. 3,856,708.

The process according to the invention characteristically employs adsorbents having a volume of pores with a diameter greater than 80 Å of more than 0.15 cm$^3$/g, preferably more than 0.3 cm$^3$/g and, even more preferably, of more than 0.4 cm$^3$/g.

The volume of pores with a diameter greater than 80 Å represents the cumulative volume of all of the pores having a size greater than a diameter of 80 Å. This volume is measured by the mercury penetration technique in which Kelvin's Law is applied.

In the event of shaping by coagulation into droplets, the particle size corresponds to the diameter of the beads; in the case of extrudates, it corresponds to their cross-sectional diameter, and in the case of crushed forms, it corresponds to the length of their larger section. In general, the adsorbents employed have a particle size of less than 4 mm. In the case of beads shaped by coagulation into droplets or of extrudates, it is advantageous to employ adsorbents having a particle size of less than 3 mm, and, even more advantageously, less than 2.4 mm.

Preferably, the process according to the invention employs adsorbents comprising at least one compound of an element selected from among the alkali metals and alkaline earth metals.

Such at least one compound can be an oxide, a hydroxide, a salt, or a mixture of these. Exemplary thereof are the hydroxides, sulfates, nitrates, halides, acetates, formates and carbonates and, more generally, the carboxylic acid salts.

Preferably, compounds of sodium, potassium and calcium are employed.

The content of the at least one compound of the alkali metals and alkaline earth metals advantageously ranges from 15 mmol to 750 mmol per 100 g of alumina, preferably from 15 to 500 mmol per 100 g of alumina, and still more preferably from 15 to 150 mmol.

These compounds can be incorporated according to the technique described in EP-A-0,379,394.

According to a first, preferred embodiment of the invention, crushed forms of alumina are used which have a specific surface area of greater than 200 m$^2$/g. This specific surface area is a BET surface area. By the term "BET surface area" is intended the specific surface area determined by adsorption of nitrogen in accordance with ASTM standard D 3663-78, established on the basis of the Brunauer-Emmett-Teller technique described in *Journal of the American Chemical Society*, 60, 309 (1938).

In the event that the process employs adsorbents obtained by crushing, such adsorbents preferably have a specific surface area of greater than 200 m$^2$/g.

When the process according to the invention employs beads or extrudates, these advantageously have a specific surface area of at least 20 m$^2$/g.

The process according to the invention attains improved degrees of adsorption of the chelated organometallic compounds of 75% and even greater. This degree of adsorption represents the proportion of metal adsorbed by the beads relative to the initial amount of metal introduced into the reaction medium, under the conditions of the adsorption test described below.

The present invention more particularly features the process employing the adsorbents described above for the adsorption of any chelated organometallic compound, more particularly those based on metals selected from among the metals of Groups IVB, VB, VIB, VIIB, VIII, IB and IIB of the Periodic Table, even more particularly those based on vanadium, titanium, zirconium or copper.

The process according to the invention is particularly well suited for the adsorption of any organometallic compound which has been chelated by organic compounds such as acetylacetone, 2-ethylhexane-1,3-diol or di-2-ethylhexyl phosphate.

Consequently, the process of the invention is suitable for the purification of polyolefins prepared via polymerization of olefins in the presence of a coordination catalyst system. The purification process can be of the type described above, in which the adsorbents are contacted with the actual medium resulting from the polymerization. Organic compounds have been introduced into such medium beforehand.

The present invention also features alumina-based adsorbents comprising a chelated organometallic compound, said adsorbents being prepared by contacting the organometallic compounds with the alumina-based adsorbents shaped by coagulation into droplets, or by extrusion or by crushing, said adsorbents having a volume of pores with a diameter greater than 80 Å of at least 0.15 cm$^3$/g and a particle size of less than 4 mm.

In the process according to the invention, the alumina-based adsorbents are contacted with the organometallic compounds and adsorb same. Upon completion of adsorption of the organometallic compounds, the adsorbents are withdrawn from the reactor to provide alumina-based adsorbents. These are prepared via shaping by coagulation into droplets or by extrusion, or by crushing, and have a volume of pores with a diameter greater than 80 Å of at least 0.15 cm$^3$/g and a particle size of less than 4 mm, and onto which the organometallic compounds are adsorbed.

The subject adsorbents can be employed directly as supported metal catalysts in any type of precious-metal catalysis which is suited to the nature of the adsorbed metal species.

In order to further illustrate the present invention and the advantages thereof, the following specific examples are given, it being understood that same are intended only as illustrative and in nowise limitative.

Adsorption tests

In said examples to follow, the adsorption tests were conducted on adsorbents which had been activated beforehand at 300° C. for 2 hours in order to remove any trace amounts of humidity following their storage and to permit a comparison to be made of their efficiency under identical conditions.

The adsorbents were introduced into a beaker which contained vanadium chelated with acetylacetonate (VO (acac)$_2$), which was present in 200 ml of toluene at a concentration of 0.1% (by weight relative to the volume of toluene). They were maintained under stirring and in contact with the compound for 48 h at 25° C. in the absence of air. The degree of adsorption of the vanadium chelated with acetylacetonate by the alumina was measured by the change in the concentration of the solution, as determined by UV-visible spectroscopy.

EXAMPLE 1

Crushed alumina

Adsorbents 1 to 5 were prepared by crushing alumina beads obtained by shaping alumina resulting from the rapid dehydration of hydrargillite in a rotating drum.

The characteristics of these adsorbents are reported in Table I:

TABLE I

| | Type | V80 Å (cm$^3$/g) | Particle size (mm) | Specific surface area (cm$^2$/g) | Degree of adsorption |
|---|---|---|---|---|---|
| Adsorbent 1 | crushed | 0.25 | 1.3 | 343 | 91 |
| Adsorbent 2 | crushed | 0.25 | 2.1 | 343 | 85.5 |
| Adsorbent 3 | crushed | 0.25 | 2.8 | 343 | 79 |
| Adsorbent 4, comparative | crushed | 0.08 | 1.7 | 254 | 68 |
| Adsorbent 5, comparative | crushed | 0.25 | 4.5 | 343 | 63.5 |

It will be noted that the crushed forms of alumina having a volume of pores with a diameter greater than 80 Å of more than 0.2 cm$^3$/g and a particle size of less than 4 mm exhibit a high degree of adsorption.

EXAMPLE 2

Beads of alumina shaped by coagulation into droplets, and extruded alumina beads The adsorbents tested were shaped either by coagulation into droplets from an alumina resulting from the precipitation of an alumina gel (Adsorbent 8) or by extrusion of this alumina gel (Adsorbents 6 and 7).

The characteristics of these adsorbents are reported in Table II:

TABLE II

| | Type | V80 Å (cm³/g) | Particle size (mm) | Specific surface area (cm²/g) | Degree of adsorption |
|---|---|---|---|---|---|
| Adsorbent 6 | extruded | 0.55 | 1.2 | 211 | 89 |
| Adsorbent 7 | extruded | 0.55 | 1.6 | 212 | 80 |
| Adsorbent 8 | coagulation into droplets | 0.54 | 2.0 | 191 | 81.5 |

It will be noted that these adsorbents, which have a volume of pores with a diameter greater than 80 Å of more than 0.2 cm³/g and a particle size of less than 4 mm, exhibit a high degree of adsorption.

EXAMPLE 3

(Comparative)

Alumina beads prepared by shaping in a rotary film coater
The characteristics of these adsorbents are reported in Table III:

TABLE III

| | Type | V80 Å (cm³/g) | Particle size (mm) | Specific surface area (cm²/g) | Degree of adsorption |
|---|---|---|---|---|---|
| Adsorbent 11, comparative | film coater | 0.15 | 1.6 | 356 | 59 |
| Adsorbent 12, comparative | film coater | 0.55 | 3.2 | 100 | 68.5 |

It will be appreciated that alumina beads prepared by shaping of alumina resulting from the rapid dehydration of hydrargillite in a rotary film coater had a degree of adsorption which was less than that of the adsorbents according to the invention.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. Adsorbent alumina particulates having chelated organometallic compound values adsorbed thereon, said alumina particulates comprising coagulated droplets, extrudates or crushed particles having a volume of pores with a diameter greater than 80 Å of at least 0.15 cm³/g and a particle size of less than 4 mm.

2. The adsorbent alumina particulates as defined by claim 1, said alumina particulates comprising at least one compound of an alkali or alkaline earth metal.

3. The adsorbent alumina particulates as defined by claim 2, said alumina particulates comprising from 15 mmol to 750 mmol of said at least one compound of an alkali or alkaline earth metal per 100 g of alumina.

4. The adsorbent alumina particulates as defined by claim 1, said alumina particulates comprising crushed particles having a specific surface area of greater than 200 m²/g.

5. The adsorbent alumina particulates as defined by claim 4, said alumina particulates comprising crushed alumina beads.

6. The adsorbent alumina particulates as defined by claim 1, said alumina particulates comprising coagulated droplets having a specific surface area of at least 20 m²/g.

7. The adsorbent alumina particulates as defined by claim 1, said alumina particulates comprising extrudates having a specific surface area of at least 20 m²/g.

8. The adsorbent alumina particulates as defined by claim 1, said chelated organometallic compound values comprising at least one compound of a metal of Groups IVB, VB, VIB, VIIB, VIII, IB or IIB of the Periodic Table.

9. The adsorbent alumina particulates as defined by claim 8, said chelated organometallic compound values comprising at least one compound of vanadium, titanium, zirconium or copper.

10. The adsorbent alumina particulates as defined by claim 8, said chelated organometallic compound values comprising a chelating agent selected from among acetylacetone, 2-ethylhexane-1,3-diol and di-2-ethylhexyl phosphate.

11. The adsorbent alumina particulates as defined by claim 1, said alumina particulates having a volume of pores with a diameter greater than 80 Å of at least 0.3 cm³/g.

12. The adsorbent alumina particulates as defined by claim 11, said alumina particulates having a volume of pores with a diameter greater than 80 Å of at least 0.4 cm³/g.

13. The adsorbent alumina particulates as defined by claim 1, said alumina particulates having a particle size of less than 3 mm.

14. The adsorbent alumina particulates as defined by claim 13, said alumina particulates having a particle size of less than 2.4 mm.

15. A process for the preparation of the adsorbent alumina particulates as defined by claim 1, comprising intimately contacting said alumina particulates with said chelated organometallic compound values.

16. A catalyst comprising the adsorbent alumina particulates as defined by claim 1.

17. A process comprising adsorbing chelated organometallic compound values from a medium of polymerization by contacting said medium with the adsorbent alumina particulates as defined by claim 1.

18. The adsorbent alumina particulates as defined by claim 1, said alumina particulates having been prepared by coagulation into droplets of an aqueous dispersion or suspension of alumina or of a solution of a basic aluminum salt in the form of an emulsion comprising an organic phase, an aqueous phase and a surfactant or emulsifier.

19. The adsorbent alumina particulates as defined by claim 1, said alumina particulates having been prepared by kneading alumina mixed with at least one pore-forming agent followed by extrusion of the kneaded mixtures.

20. The adsorbent alumina particulates as defined by claim 1, said alumina particulates having been prepared by contacting alumina-based adsorbents with organometallic compounds so as to absorb the organometallic compounds on the adsorbents followed by shaping the adsorbents into said particulates by coagulation into droplets, extrusion or crushing.

* * * * *